(12) United States Patent
Inaniwa et al.

(10) Patent No.: US 9,795,807 B2
(45) Date of Patent: Oct. 24, 2017

(54) IRRADIATION PLANNING APPARATUS AND CHARGED PARTICLE IRRADIATION SYSTEM

(71) Applicant: NATIONAL INSTITUTES FOR QUANTUM AND RADIOLOGICAL SCIENCE AND TECHNOLOGY, Chiba-shi, Chiba (JP)

(72) Inventors: Taku Inaniwa, Chiba (JP); Nobuyuki Kanematsu, Chiba (JP); Takuji Furukawa, Sakura (JP); Toshiyuki Shirai, Narashino (JP); Koji Noda, Narashino (JP)

(73) Assignee: NATIONAL INSTITUTES FOR QUANTUM AND RADIOLOGICAL SCIENCE AND TECHNOLOGY, Chiba-shi (JP)

( * ) Notice: Subject to any disclaimer, the term of this patent is extended or adjusted under 35 U.S.C. 154(b) by 351 days.

(21) Appl. No.: 14/399,714

(22) PCT Filed: Apr. 16, 2013

(86) PCT No.: PCT/JP2013/002564
§ 371 (c)(1),
(2) Date: Nov. 7, 2014

(87) PCT Pub. No.: WO2013/168362
PCT Pub. Date: Nov. 14, 2013

(65) Prior Publication Data
US 2015/0133714 A1    May 14, 2015

(30) Foreign Application Priority Data
May 7, 2012    (JP) .................. 2012-106365

(51) Int. Cl.
*A61N 5/10* (2006.01)
*G21K 5/04* (2006.01)
*G21K 1/08* (2006.01)

(52) U.S. Cl.
CPC ........... *A61N 5/1075* (2013.01); *A61N 5/103* (2013.01); *A61N 5/1079* (2013.01); *G21K 5/04* (2013.01);
(Continued)

(58) Field of Classification Search
CPC .. A61N 5/1043; A61N 5/1075; A61N 5/1079; A61N 2005/1087; G21K 1/08; G21K 5/04
See application file for complete search history.

(56) References Cited

U.S. PATENT DOCUMENTS 8,183,541 B2    5/2012  Wilkens et al.
2009/0304154 A1*  12/2009  Lomax ............... A61N 5/103
                                                378/65
(Continued)

FOREIGN PATENT DOCUMENTS

JP    2000-202047    7/2000
JP    2000-354637    12/2000
(Continued)

*Primary Examiner* — Charles A Marmor, II
*Assistant Examiner* — Thaddeus Cox
(74) *Attorney, Agent, or Firm* — Hamre, Schumann, Mueller & Larson, P.C.

(57) ABSTRACT

A planning apparatus (70) determines irradiation parameter data (67) for a charged particle irradiation system (1), which radiates charged particles generated by an ion source (2) to a target (80) by accelerating the charged particles by means of a linear accelerator (4) and a synchrotron (5). The planning apparatus is provided with: a planning program (73), which determines the irradiation parameter data (67) with respect to one target (80) by combining charged particles of a plurality of kinds of ion species; and a CPU (71)
(Continued)

for executing the planning program. Consequently, the irradiation planning apparatus capable of performing irradiation with desirable dose distribution with respect to the target, the irradiation planning program, an irradiation plan determining method, and the charged particle irradiation system are provided.

8 Claims, 4 Drawing Sheets

(52) U.S. Cl.
CPC .......... *A61N 5/1043* (2013.01); *A61N 5/1071* (2013.01); *A61N 2005/1087* (2013.01); *G21K 1/08* (2013.01)

(56) References Cited

U.S. PATENT DOCUMENTS

| | | | |
|---|---|---|---|
| 2010/0088339 A1 | 4/2010 | Rietzel et al. | |
| 2012/0241635 A1* | 9/2012 | Luechtenborg | A61N 5/1043 250/389 |
| 2013/0092839 A1* | 4/2013 | Kraft | A61N 5/1043 250/360.1 |

FOREIGN PATENT DOCUMENTS

| | | |
|---|---|---|
| JP | 2009-525797 | 7/2009 |
| JP | 2010-51811 | 3/2010 |

* cited by examiner

IRRADIATION PLANNING APPARATUS AND CHARGED PARTICLE IRRADIATION SYSTEM

TECHNICAL FIELD

The present invention relates to an irradiation planning apparatus for making, for example, an irradiation plan for a charged particle irradiation system that radiates charged particles to a target, an irradiation planning program, an irradiation plan determining method, and a charged particle irradiation system.

BACKGROUND ART

Conventionally, there have been proposed an apparatus that conducts a heavy charged particle therapy by radiating charged particles to an affected area such as cancer cells. In a heavy charged particle therapy such as a carbon filament therapy, it is desirable to realize a uniform clinical effect in the target. For achieving this, it is possible to define a clinical dose which is the product of an absorbed dose and a relative biological effectiveness (RBE), and make an irradiation plan so that the clinical dose is uniform in the target.

Figure 4:
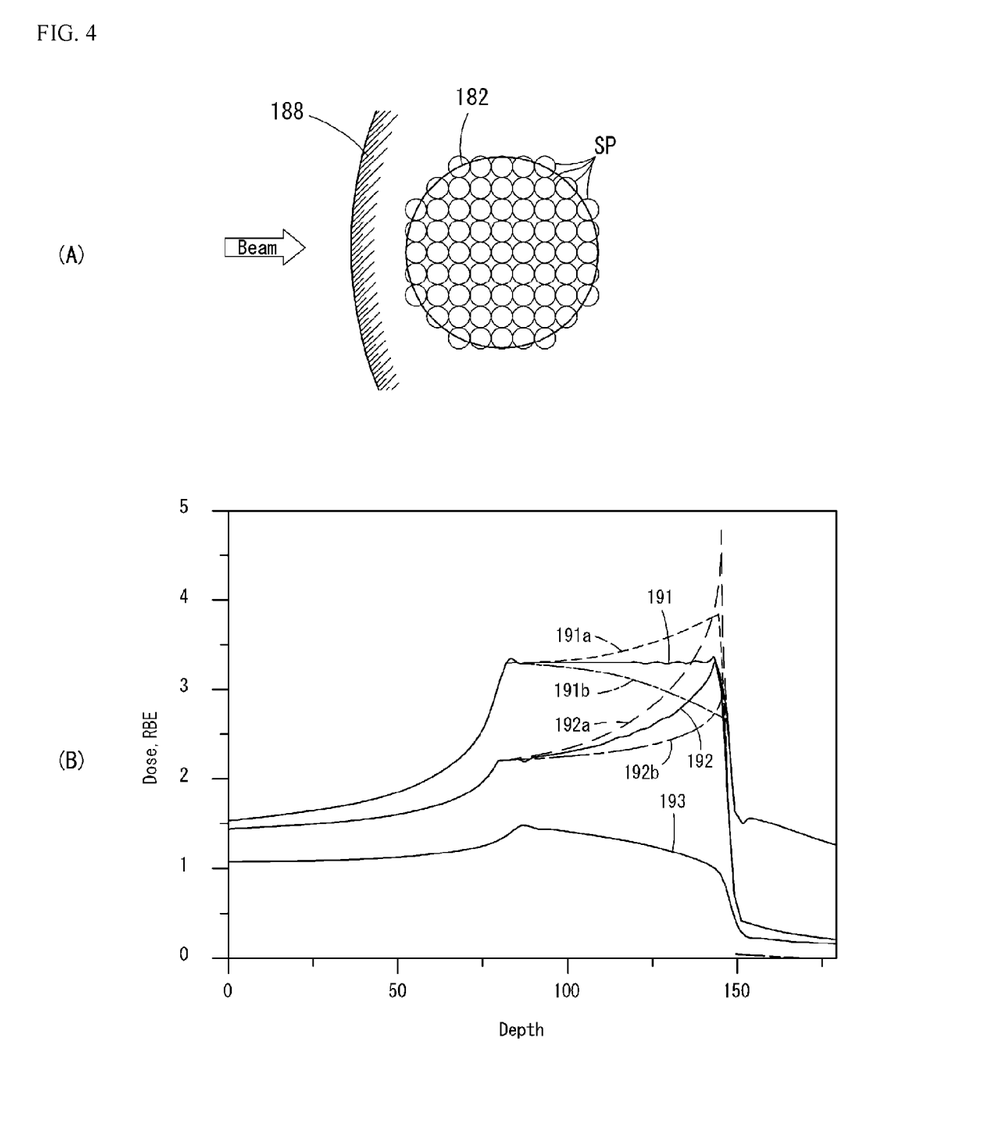
FIG. 4 is a diagram illustrating conventional ion species irradiation, and its effect.

FIG. 4(A) is a diagram illustrating irradiation spots to which charged particles of a single ion species are to be radiated. FIG. 4(A) shows a longitudinal section of a target viewed from the lateral side of the traveling direction of the beam. In the apparatus that conducts a heavy charged particle therapy, as illustrated in the drawing, spots SP disposed on the surface perpendicular to the irradiation direction are arranged in the irradiation direction with respect to a tumor region 182 located behind a body surface 188, and thus the spots SP are arranged three-dimensionally. The apparatus that conducts a heavy charged particle therapy sequentially radiates a beam of ion species to the spots SP from the direction of the arrow illustrated in the drawing and conducts irradiation in a manner of filling the tumor region 182.

FIG. 4(B) illustrates a depth dose distribution chart by such a carbon filament therapy. In this chart, depth distributions of a clinical dose 191, an RBE 192, and an ion species irradiation dose 193 are shown. In designing a clinical dose that is uniform in the target in the carbon filament therapy, the quality (LET) distribution of carbon filament for realizing this is determined almost uniquely. Here, when the RBE 192 involves errors 192a, 192b, large distortions 191a, 191b occur in the distribution of the clinical dose 191, and the clinical dose distribution can greatly deteriorate.

RBE depends on quality of radiation (particle species or LET), dose level, cell strain, end point and so on, and RBE itself is accompanied by a large error. Therefore, it is desired to reduce the error in RBE for preventing significant deterioration in the clinical dose distribution.

There have been proposed a method and an apparatus for charged particle beam irradiation capable of radiating charged particles from a plurality of directions by having a rotary irradiation device (see Patent Document 1). With this apparatus, since charged particles can be radiated from the plurality of directions, it is possible to reduce the irradiation dose on normal sites by widely dispersing the dose to be radiated to the normal sites. Radiation of the charged particles from the plurality of directions can also reduce an error in RBE.

Increased irradiation directions, however, lead to several disadvantages. First, increased irradiation directions disadvantageously increase a burden on a staff engaged in the therapy. In addition, increased irradiation directions disadvantageously lead to a large increase in exposure volume of normal tissues. There is a disadvantage that a rotary gantry like a rotary irradiation device of Patent Document 1 is bulky. Also, there is a disadvantage that a rotary gantry for heavy charged particles has not been practically used in an actual therapy because of difficulties in its construction and operation.

Besides the above, since occurrence of a delayed effect such as cerebral necrosis from the planned therapeutic volume (PTV) after the therapy is reported for part of sites such as a cerebral tumor, it is desired to develop an irradiation method capable of effectively controlling only cancer cells without injuring normal cells contained in a tumor.

PRIOR ART DOCUMENT

Patent Document

Patent Document 1: Japanese Patent Laid-open Publication No. 2000-202047

SUMMARY OF THE INVENTION

Problems to be Solved by the Invention

In light of the above problems, it is an object of the present invention to provide an irradiation planning apparatus, an irradiation planning program, an irradiation plan determining method, and a charged particle irradiation system capable of realizing irradiation with desirable dose distribution with respect to a target.

Solutions to the Problems

The present invention provides an irradiation planning apparatus for determining an irradiation parameter of a charged particle irradiation system that radiates charged particles generated by an ion source to a target by accelerating the charged particles by means of an accelerator, the irradiation planning apparatus having composite irradiation parameter determining means that determines the irradiation parameter with respect to one target by combining the charged particles of a plurality of kinds of ion species, or an irradiation planning program, an irradiation plan determining method, and a charged particle irradiation system for the irradiation planning apparatus.

Effects of the Invention

In the present invention, it is possible to provide an irradiation planning apparatus, an irradiation planning program, an irradiation plan determining method, and a charged particle irradiation system capable of achieving irradiation with desirable dose distribution with respect to one target.

EMBODIMENTS OF THE INVENTION

Hereinafter, one embodiment of the present invention will be described by referring to the attached drawings.

Figure 1:
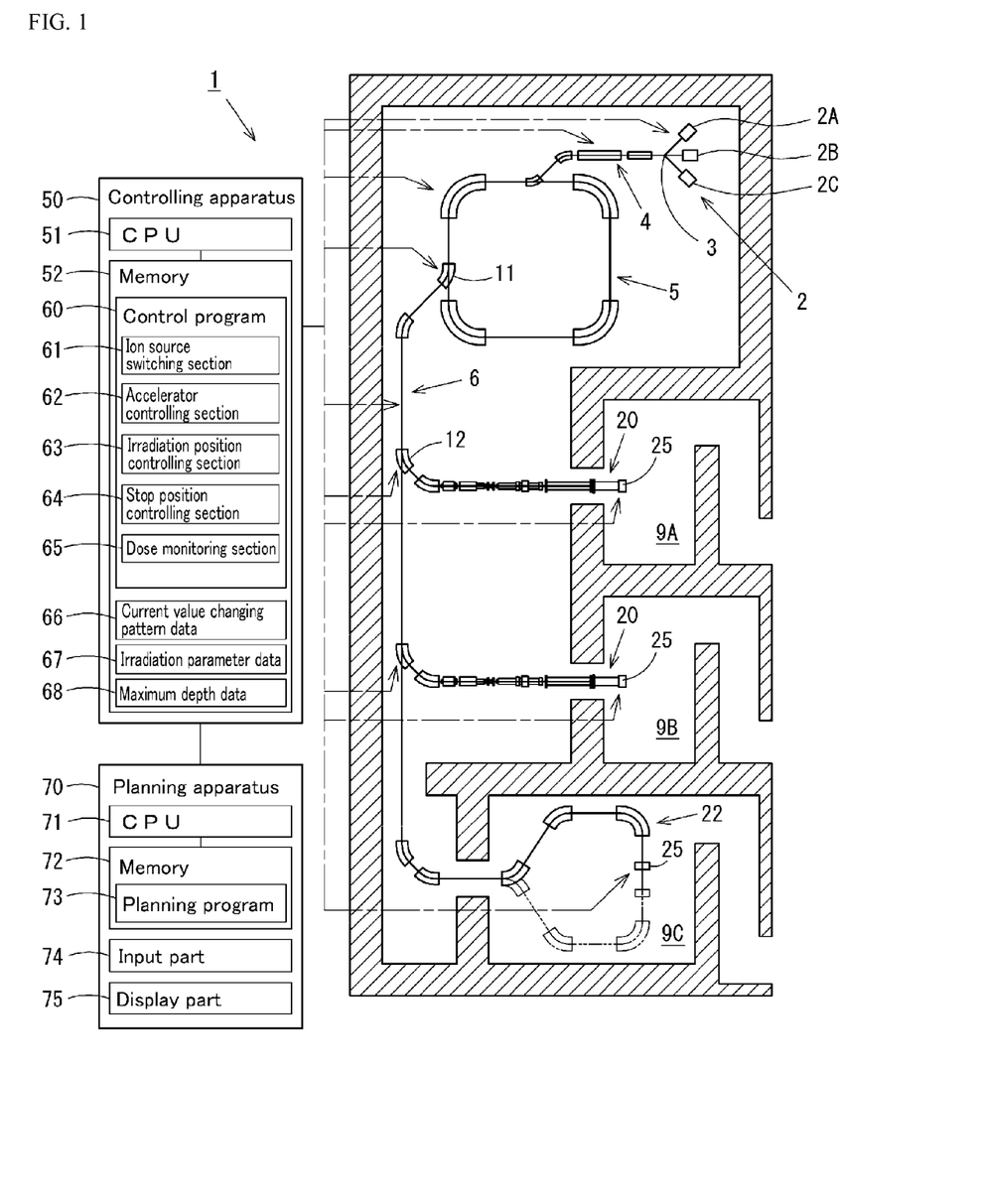
FIG. 1 is a block diagram showing a configuration of a charged particle irradiation system.

FIG. 1 is a block diagram showing a configuration of a charged particle irradiation system 1. The charged particle irradiation system 1 includes a plurality of ion sources 2 (2A, 2B, 2C), a multiple ion source connector 3, a linear accelerator 4, a synchrotron 5, a conveyance system 6, a fixed radiator 20, a rotary gantry 22, and a controlling apparatus 50 for controlling these. To the controlling apparatus 50, a planning apparatus 70 that transmits therapy planning data is connected.

The ion source 2 is a device that removes an electron from an atom to generate an ion, and includes a first ion source 2A for drawing an ion species of the first kind, a second ion source 2B for drawing an ion species of the second kind, and a third ion source 2C for drawing an ion species of the third kind. The first to third ion sources 2 are configured to generate different kinds of ions, e.g., oxygen ions, carbon ions, and helium ions, respectively.

The multiple ion source connector 3 is a connector that selectively connects the first ion source 2A to the third ion source 2C to the linear accelerator 4. The multiple ion source connector 3 appropriately switches the ion source 2 for supplying the linear accelerator 4 with ion species, to any one of the first ion source 2A to the third ion source 2C under the control by the controlling apparatus 50.

The linear accelerator 4 is a kind of accelerator, and accelerates the charged particles supplied from the ion source 2 to have a predetermined energy by means of an electromagnet, and supplies the charged particles to the synchrotron 5.

The synchrotron 5 is a kind of accelerator, and further accelerates the charged particles incident from the linear accelerator 4 on a circling orbit by means of an electromagnet to make the charged particles have high energy.

The conveyance system 6 conveys the charged particles drawn by an emitter 11 from the synchrotron 5 to an irradiation device 25 by means of an electromagnet.

The emitter 11 is provided at a connecting part between the synchrotron 5 and the conveyance system 6, and emits the charged particles to the conveyance system 6 from the synchrotron 5 under the control by the controlling apparatus 50.

A switch 12 is provided on the conveyance system 6, and switches the therapy rooms 9 (9A, 9B, 9C) accommodating the irradiation device 25 to which the charged particles conveyed by the conveyance system 6 are to be conveyed under the control by the controlling apparatus.

The fixed radiator 20 provided in each of the therapy rooms 9A, 9B radiates charged particles from the irradiation device 25 provided at its trailing end.

The rotary gantry 22 provided in the therapy room 9C can change the irradiation direction of charged particles by rotation, and radiates charged particles from the irradiation device 25 at the trailing end toward the changed irradiation direction.

The irradiation device 25 controls a position in the XY direction of charged particles (planar direction perpendicular to the radiation direction of charged particles) by means of a X-direction scanning magnet and a Y-direction scanning magnet, and controls a stop position in the Z direction of charged particles (traveling direction of charged particles) by means of an energy changing part (range shifter), and measures the irradiation dose of charged particles for each irradiation spot by means of a scanning monitor. In other words, the irradiation device 25 functions as a scanning irradiation device that controls the three-dimensional position of an irradiation spot of charged particles while measuring the irradiation dose. This scanning irradiation device three-dimensionally scans a pencil beam in which charged particles are narrowed down, and conducts a therapy in a manner of filling the tumor.

The controlling apparatus 50 has a CPU (central processing unit) 51 and a memory 52. The memory 52 stores various programs and data including a control program 60, current value changing pattern data 66, irradiation parameter data 67, and maximum depth data 68. The CPU 51 operates by using the data such as the current value changing pattern data 66, and the irradiation parameter data 67 in accordance with the program such as the control program 60. By this operation, the controlling apparatus 50 functions as an ion source switching section 61, an accelerator controlling section 62, an irradiation position controlling section 63, a stop position controlling section 64, and a dose monitoring section 65. The CPU 51 also functions as a multiple ion species irradiation controller that conducts a control of making the ion source switching section 61 switch the ion species, making the accelerator controlling section 62 accelerate with an appropriate current, and making the irradiation position controlling section 63 and the stop position controlling section 64 sequentially change the irradiation spot.

The ion source switching section 61 conducts a control of switching the ion source for generating charged particles to either one of the first ion source 2A to the third ion source 2C. This makes it possible to switch the ion species between spills.

The accelerator controlling section 62 reads out an appropriate current value changing pattern from the current value changing pattern data 66 in accordance with the ion species supplied from the ion source 2, and controls the current value to be flown in the electromagnet of the accelerator 4 in accordance with this current value changing pattern.

The irradiation position controlling section 63 controls and drives the X-direction scanning magnet and the Y-direction scanning magnet of the irradiation device 25 to control the position in the plane perpendicular to the traveling direction (position in the XY direction) of charged particles to be emitted to the target.

The stop position controlling section 64 controls and drives the energy changing part of the irradiation device 25 to control the stop position of charged particles in the traveling direction of the charged particles (Z direction).

The dose monitoring section 65 acquires an irradiation dose for each irradiation spot measured by a dose monitor of the irradiation device 25.

The current value changing pattern data 66 is pattern data of current values to be flown in the electromagnets of the linear accelerator 4, the synchrotron 5, and the linear accelerator 4 for individual ion species. The memory 52 storing the current value changing pattern data 66 functions as a current pattern memory.

The irradiation parameter data 67 is data including spot number, X position, Y position, energy, irradiation amount, and ion species. The energy indicates an irradiation position in the Z direction. The irradiation amount indicates the number of charged particles to be radiated, or a dose. The ion species consists of appropriate information from which the ion species to be radiated can be identified, for example, ion species name, ion species number, or ion source ID indicating which one of the first ion source 2A to the third ion source 2C is to be used as the ion source. The irradiation parameter data 67 is received from the planning apparatus 70 and stored in the memory 52.

The maximum depth data 68 stores maximum depths of individual ion species that can be radiated by the charged particle irradiation system 1. These maximum depths are smaller in heavier ion species, and larger in lighter ion species. Therefore, the settings may be provided not for light ion species, but only for part of heavy ion species that can be used.

Besides the above, the controlling apparatus 50 also executes a control of emitting charged particles from the emitter 11 and a control of switching the destination of irradiation of charged particles by the switch 12.

The switching of the irradiation spot and the switching of the ion species by the controlling apparatus 50 may be conducted in an appropriate order. For example, after completion of irradiation to all the irradiation spots with one ion species, the ion species may be switched to the next ion species, or after irradiating a predetermined range of irradiation spots with all ion species, the irradiation spots may be switched to the next predetermined range of irradiation spots. The predetermined range of irradiation spots can be appropriately set in such a manner that it is the whole of the irradiation spots in the plane perpendicular to the irradiation direction at one depth position of the irradiation direction, or it is one irradiation spot. Since it is necessary to change the current value to be flown in the synchrotron 5 or the like in accordance with the current value changing pattern data 66 when the ion species is changed, it is desired to irradiate all the irradiation spots sequentially with each ion species.

This charged particle irradiation system 1 allows generation of the charged particles of the plurality of kinds of different ion species by the ion source 2, and allows irradiation of one target with accelerated charged particles of various ion species while switching the plurality of kinds of ion species.

The planning apparatus 70 is a computer having a CPU 71, a memory 72, an input part 74, and a display part 75, and functions as an irradiation planning apparatus or a therapy planning apparatus.

The memory 72 stores various programs including a planning program 73 as an irradiation planning program, and various data.

The CPU 71 operates using data in the memory 72 in accordance with a program such as the planning program 73. By this operation, the planning apparatus 70 generates the irradiation parameter data 67, and transmits the irradiation parameter data 67 to the controlling apparatus 50.

The input part 74 is configured by input devices such as a keyboard and a mouse, and receives an input operation, for example, by a person who is planning the therapy.

The display part 75 is configured by a display device such as a display for displaying characters and images, and displays various images including CT captured image, MRI image and PET image, and various regions (GTV, CTV, PTV) and so on.

By means of the charged particle irradiation system 1 configured as described above, it is possible to execute an intensity modulated composite ion therapy (IMCIT) that radiates charged particles while modulating the beam intensity by using a plurality of kinds of ion species based on the irradiation parameter data 67.

Next, an operation for creating the irradiation parameter data 67 using a plurality of kinds of ion species by the planning apparatus 70 will be described.

The intensity modulated composite ion therapy of the present invention sequentially determines "which ion species m", "to which spot i", and "how many $w_{i,m}$" is to be radiated, by inverse planning. The spot i indicates the spot number of the irradiation parameter data 67.

First, the planning apparatus 70 selects the number of ion species M to be radiated, and the ion species, and creates a dose kernel for irradiation of each spot for each ion species. The dose kernel $d_{i,m}(r)$ indicates a dose applied to a position r in a patient body by a pencil beam of ion species m radiated to the spot i. The dose kernel $d_{i,m}(r)$ reflects physical characteristics of each ion species. The physical characteristics used herein include extension of beam due to scattering, and an amount of generated fragments, and LET (Linear Energy Transfer).

In a therapy planning of the intensity modulated composite ion therapy, it is possible to determine the irradiation parameters $(w_{i,m})$ for the purpose by formulating the evaluation index f of the repetitive operation by a least square method or the like depending on the purpose.

<1> First Evaluation Index f

As the first example, an evaluation index f can be calculated by Mathematical formula 1 and Mathematical formula 2 below.

$$f(w_m) = \sum_{j \in T} \left( Q_T^o H' \left[ \sum_{m=1}^{M} D_j(w_m) - D_T^{max} \right]^2 + Q_T^u H' \left[ D_T^{min} - \sum_{m=1}^{M} D_j(w_m) \right]^2 \right) + \sum_{j \in O} Q_O^o H' \left[ \sum_{m=1}^{M} D_j(w_m) - D_O^{max} \right]^2 \quad \text{[Mathematical formula 1]}$$

$$D_j(w_m) = \sum_{i=1}^{N} d_{i,m}(r_j) w_{i,m} \equiv \sum_{i=1}^{N} d_{i,m} w_{i,m} \quad \text{[Mathematical formula 2]}$$

The evaluation index f represented by [Mathematical formula 1] consists of three terms. The first term and the second term are operations for a target. The target used herein refers to an irradiation region that is determined based on a tumor-invasion region specified by a physician or the like while an irradiation error or the like is taken into account. The third term is an operation for OAR (Organ At Risk).

The first term represents a penalty for the value over the maximum allowable value, and is multiplication of $Q_T^O$ and H' [(subtraction)]$^2$. The (subtraction) part is a formula that subtracts a maximum dose $D_T^{max}$ which is the maximum allowable value, from a dose applied to each position j (three-dimensional position in the patient body, preferably specified with higher resolution than the resolution for the position specified by the spot i) of the target when $w_m$ nuclides of a plurality of kinds of ion species m are radiated. The H' [ ] part represents a Heaviside function, and the value is fetched when the value of the (subtraction) part is positive, and zero is assigned when it is negative. Therefore, when the dose is less than or equal to the maximum allowable value, the first term is zero which is assigned for an appropriate value, and does not increase the evaluation index f. $Q_T^O$ is a penalty coefficient, and when it is set large, the value over the maximum allowable value calculated by H' [(subtraction)]$^2$ greatly influences the evaluation index f.

The second term represents a penalty for the value under the minimum allowable value, and is multiplication of $Q_T^U$ and H' [(subtraction)]². The (subtraction) part is a formula that subtracts a dose applied to each position j (three-dimensional position in the patient body) of the target when $w_m$ nuclides of a plurality of kinds of ion species m are radiated from a minimum dose $D_T^{min}$ which is the minimum allowable value. The H' [ ] part does not increase the evaluation index f when the dose is more than or equal to the minimum allowable value because the second term is zero which is assigned for an appropriate value. $Q_T^U$ is a penalty coefficient, and when it is set large, the value under the minimum allowable value calculated by H' [(subtraction)]² greatly influences the evaluation index f.

The third term represents a penalty for the value over the maximum allowable value of dose that can be radiated to organ at risk, and is multiplication of $Q_O^O$ and H' [(subtraction)]². The (subtraction) part is a formula that subtracts a maximum dose $D_O^{max}$ which is the maximum allowable value, from a dose applied to each position j (three-dimensional position in the patient body) of the target when $w_m$ nuclides of a plurality of kinds of ion species m are radiated. The H' [ ] part does not increase evaluation index f when the dose is less than or equal to the maximum allowable value because the first term is zero which is assigned for an appropriate value. $Q_T^O$ is a penalty coefficient, and when it is set large, the value over the maximum allowable value calculated by H' [(subtraction)]² greatly influences the evaluation index f.

For example, assuming the case where a peripheral region of the target is set as OAR, and coefficient of a risk degree $Q_O^O$ of the third term is set at a large value, the number $w_{i,m}$ of ion species m to be radiated to each spot i is optimally determined so that the evaluation index f ($w_m$) is minimum in the inverse planning that inversely calculates an optimum irradiation method from the optimum dose distribution.

Therefore, by setting the coefficient of risk degree $Q_O^O$ at a large value, it is possible to determine "to which position", "with which ion species", and "how much" irradiation is to be made for minimizing the dose application to the peripheral region of the target while keeping a necessary and sufficient dose (first term, second term) for the target.

By using the first evaluation index f, it is possible to increase dose concentration to the tumor, compared with the conventional example where only one kind of ion species is used.

<2> Second Evaluation Index f

As a second example, an evaluation index f can be calculated by Mathematical formula 3 below.

$$f(w_m) = \sum_{j \in T} \left( Q_T^o H' \left[ \sum_{m=1}^{M} D_j(w_m) - D_T^{max} \right]^2 + Q_T^u H' \left[ D_T^{min} - \sum_{m=1}^{M} D_j(w_m) \right]^2 \right) + \sum_{j \in T'} Q_T^o H' [LET_{T'}^{min} - LET_j(w_{m=1,M})]^2$$ [Mathematical formula 3]

The third term of [Mathematical formula 3] represents a penalty for the case where the irradiation amount to a region T' of high-grade tumor is less than the minimum allowable value, and is multiplication of $Q_T^{'O}$ and H' [(subtraction)]². The (subtraction) part is a formula that subtracts an energy amount LET applied to each position j (three-dimensional position in the patient body) of the target when $w_m$ nuclides of a plurality of kinds of ion species m are radiated, from a minimum energy amount $LET_{T'}^{min}$ which is the minimum allowable value. The H' H part does not increase the evaluation index f when the dose is more than or equal to the minimum allowable value because the third term is zero which is assigned for an appropriate value. $Q_T^O$ is a penalty coefficient, and when it is set large, the value under the minimum allowable value calculated by H' [(subtraction)]² greatly influences the evaluation index f.

By adding the third term of [Mathematical formula 3] as described above, it is possible to provide a limit that prevents LET of a partial region (T') in the tumor from being lower than a certain value $LET_{T'}^{min}$.

By using the second evaluation index f, it is possible to provide an effective therapy in accordance with, for example, difference in radiation sensitivity between normal cells and cancer cells contained in the tumor.

<3> Third Evaluation Index f

As the third example, an evaluation index f can be calculated by the following Mathematical formula 4.

$$f(w_m) = \int_{\alpha_{min}}^{\alpha_{max}} \sum_{j \in T} \left( Q_T^o H' \left[ \sum_{m=1}^{M} D_j(\alpha, w_m) - D_T^{max} \right]^2 + Q_T^u H' \left[ D_T^{min} - \sum_{m=1}^{M} D_j(\alpha, w_m) \right]^2 \right) \phi(\alpha) d\alpha$$ [Mathematical formula 4]

In [Mathematical formula 4], parameter a defining a biological effect is varied within the range of assumed errors $\alpha_{min} \leq \alpha \leq \alpha_{max}$, and a weight $w_m$ for each ion species with which dose distribution in the target falls within the allowable values shown by the following mathematical formula [5] for every a is optimally determined for individual ion species. Here, $\phi(\alpha)$ represents probability (probability density function) of assuming α.

$$D_T^{min} \leq \sum_{m=1}^{M} D_j(\alpha, w_m) \leq D_T^{max}$$ [Mathematical formula 5]

By using this third evaluation index f, it is possible to provide a robust therapy that is insusceptible to relative biological effectiveness (RBE) and irradiation, and registration error.

<4> Setting of Depth Limit for Individual Ion Species

A dose kernel cannot be created for a depth exceeding the maximum accelerable energy for ion species (nuclide). For this reason, maximum depths for individual ion species are registered in the maximum depth data 68, and ion species that are selectable are limited. As a result, for the depth exceeding the maximum accelerable energy for a certain ion species, an ion species that is lighter than the certain ion species is radiated. For example, in a facility having a synchrotron capable of radiating 16 cm for oxygen, 22 cm for carbon, and 66 cm for helium, the position exceeding 22 cm is automatically irradiated with helium by registering the specification in the therapy plan, and imposing the limitation.

As a result, the advantages of lower prices and smaller sizes of the heavy charged particle therapy apparatus equipped with the charged particle irradiation system 1 are obtained.

By formulating the objective functions of inverse planning in conformance with the purpose as shown in <1> to <4> with the use of the flexibility associated with the use of a plurality of kinds of ion species, it is possible to automatically determine irradiation parameters that are consistent with the purpose.

Figure 2:
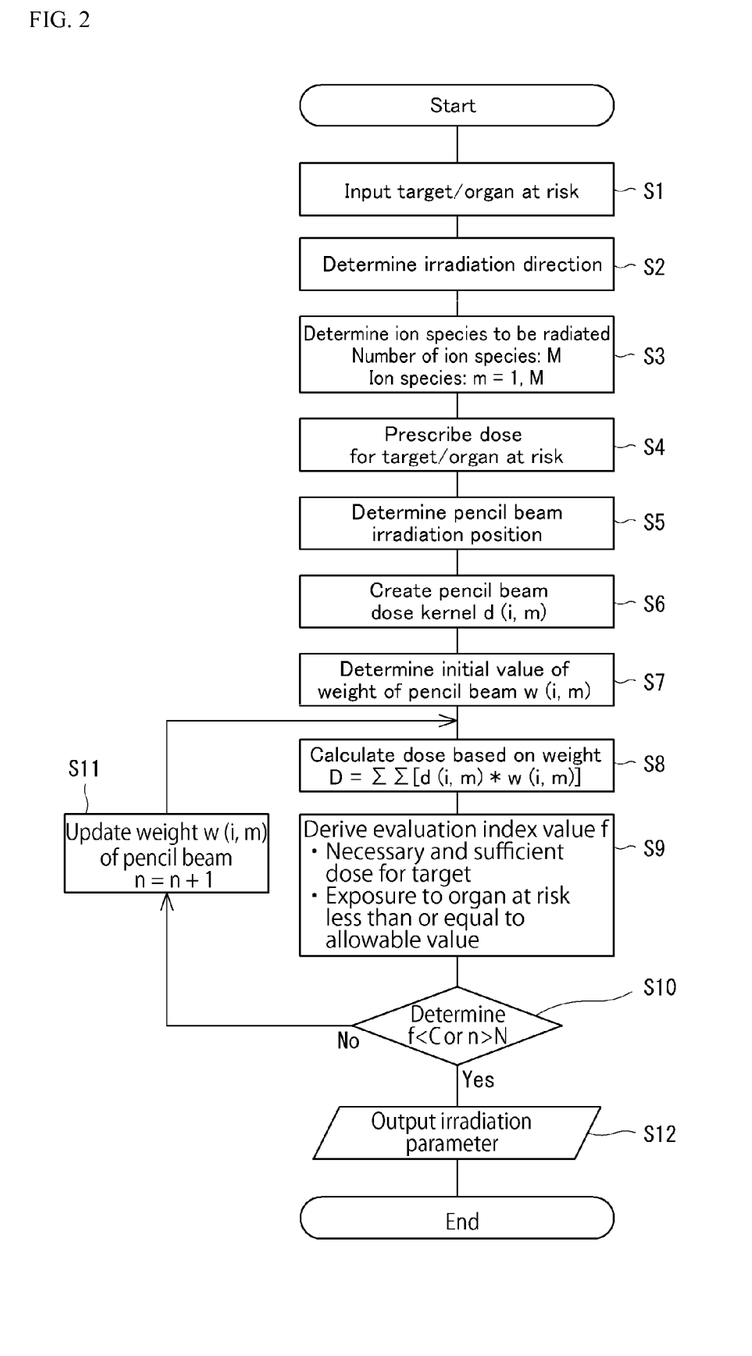
FIG. 2 is a flowchart of a planning program executed by a CPU of a planning apparatus.

FIG. 2 is a flowchart of a process executed by the CPU 71 of the planning apparatus 70 to generate the irradiation parameter data 67 in accordance with the planning program 73. The CPU 71 executing this process functions as composite irradiation parameter determining means.

First, the CPU 71 receives input of data about target/organ at risk based on data obtained by separate CT imaging from the input part 74 (step S1). This data input is made by a physician, for example by surrounding respective regions of GTV and CTV in a CT captured image displayed in the display part 75. GTV is a macroscopic tumor volume that can be observed in an image or by palpation, whereas CTV is a clinical target volume including GTV and a microscopic progression range. At this time, the planning apparatus 70 also permits input of an allowable evaluation value C for which the evaluation index f is a sufficiently small value.

The CPU 71 determines an irradiation direction in which a pencil beam is radiated for the input data of target/organ at risk (step S2). This determination can be achieved by appropriate methods including input by an operator, or determination by the CPU 71 in accordance with a preset algorism for determining an irradiation direction.

The CPU 71 determines an ion species to be radiated (step S3). Here, the number of ion species is determined as M, and ion species is determined as m=1, M. Since this determination of ion species depends on the ion species that can be radiated from the ion source 2, the determination may be made by reading out data of the ion species that can be radiated, preliminarily stored in the memory 72 of the planning apparatus 70. The determination may be conducted by an appropriate method, for example, by inputting a plurality of kinds of ion species (for example, three kinds) to be used among a plurality of kinds of ion species (for example, four kinds) that are selectable in the charged particle irradiation system 1, by a therapy planner, or by an appropriate algorism.

The CPU 71 prescribes doses for a target/organ at risk (step S4). Here, a therapy planner inputs a maximum allowable value Dmax, a minimum allowable value Dmin and the like shown in [Mathematical formula 1] to [Mathematical formula 5] at the input part 74 under a physician's direction.

The CPU 71 determines an irradiation position of a pencil beam (step S5). The irradiation position is determined by arranging beam spots densely three-dimensionally for the entire region of PTV (which is to be a target). The entire irradiation position determined in this manner is a target T, and each one of the irradiation positions is a spot to which a pencil beam of ion species is to be radiated. PTV refers to a planned target volume including CTV and an irradiation error. The CPU 71 sets the part corresponding to GTV in the irradiation position as a high-grade malignant target T', and the periphery of the irradiation position as a protective region O which is OAR.

The CPU 71 creates a dose kernel d (i, m) of a pencil beam (step S6). Here, i represents an irradiation position (spot ID), and m represents a volume.

The CPU 71 determines an initial value of a weight w (i, m) of a pencil beam (step S7). This initial value is determined by the CPU 71 on the basis of a rough order regarding the number of nuclides to be radiated to the spot.

The CPU 71 calculates a dose D based on the weight (step S8). This dose calculation gives candidates for the irradiation parameter data 67 that determines the position, the ion species, and the amount to be radiated.

The CPU 71 derives an evaluation index f so that the dose is necessary and sufficient to the target, and exposure to organ at risk is not more than allowable values (step S9).

The CPU 71 repeats steps S8 to S9 while updating the weight w (i, m) of the pencil beam and adding a variable n by 1 (step S11) until the evaluation index f is less than C or the variable n is larger than N (step S10: No). C represents an allowable evaluation value indicating that the evaluation index f is sufficiently small and allowable, and N represents the maximum number of repetition. Therefore, when the evaluation index f is less than C and is sufficiently small, or the maximum number of repetition is reached, the repetitive operation ends. As to updating of the weight w (i, m), it is desired to update the data of the entire region to be irradiated. Besides, the value currently stored and the value obtained by the calculation of this time may be compared for each spot, and the value of the spot may be updated when the value obtained by the calculation of this time is preferred.

When the evaluation index f is less than C, or the variable n is larger than N (step S10: Yes), the CPU 71 outputs the irradiation parameter data 67 to the controlling apparatus 50 (step S12), and ends the process.

Through these operations, the planning apparatus 70 can generate the irradiation parameter data 67 using a plurality of kinds of ion species. The controlling apparatus 50 of the charged particle irradiation system 1 can irradiate one target (irradiation region of one patient) with any one of the plurality of kinds of ion species switched in accordance with the irradiation parameter data 67. As described above, by having the ion sources 2A to 2C, and switching the energy and the ion species during a single irradiation from one direction by conducting switching of ion species, acceleration, drawing and irradiation, it is possible to realize any dose/dose distribution in the tumor.

Figure 3:
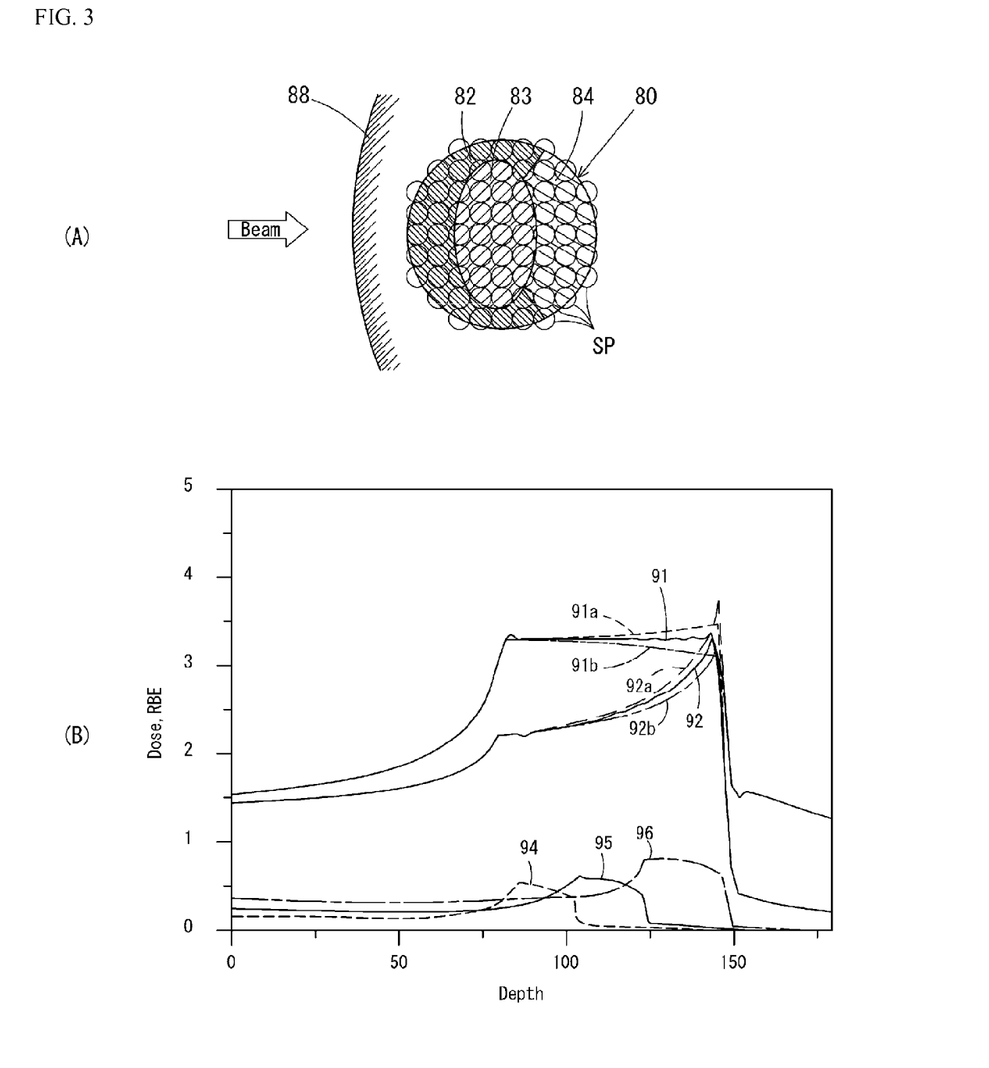
FIG. 3 is a diagram illustrating composite irradiation with a plurality of kinds of ion species, and its effect.

By the irradiation parameter data 67 thus generated, the arrangement of ion species to be radiated to the tumor is set, for example, in the manner as shown in the irradiation ion species distribution chart of FIG. 3(A). FIG. 3(A) is a longitudinal section of irradiation ion species distribution viewed from the lateral side of the beam traveling direction. Irradiation spots SP are three-dimensionally arranged so that the entire target 80 is filled. In this example, the front side of the irradiation direction (the side closer to a body surface 88) and the peripheral part in the XY direction are set as a first irradiation region 82 mainly composed of a heavy ion species (oxygen O in this example), the center part of the tumor is set as a second irradiation region 83 mainly composed of a lighter ion species (carbon C in this example), and the back side of the irradiation direction is set as a third irradiation region 84 mainly composed of a further lighter ion species (helium He in this example). By irradiating in this manner, it is possible to achieve irradiation with desired quality of radiation for each site (each of the irradiation regions 82, 83, 84) in the target 80 by combining the advantage of the heavy ion species having characteristics of small scattering, large generation quantity of fragments, and high LET, and the advantage of the light ion species having characteristics of large scattering, small generation quantity of fragments, and low LET. In brief, the charged particle irradiation system 1 can concentrate the dose at the target 80 while minimizing exposure to the peripheral normal tissues by irradiating the periphery of the target (peripheral part perpendicular to the irradiation direction) with a heavy ion species to make the scattering small, and irradiating the downstream side of the target (back side of the irradiation direction) with a light ion species to reduce the application of dose to the back side of the target due to fragments, and irradiating the upstream side of the target (front side of the irradiation direction) with a heavy ion species to make LET high.

For the irradiation regions 82, 83, 84, the irradiation setting can be made appropriately, for example, radiating a single ion species to each irradiation spot, or radiating to each irradiation spot a combination of a plurality of kinds of ion species in different proportions of irradiation amounts (the number of radiated charged particles) for different ion species, or making irradiation spots to be irradiated with a single ion species, and irradiation spots to be irradiated with a plurality of kinds of ion species coexist.

FIG. 3(B) shows a depth dose distribution chart radiated by the controlling apparatus 50 using a plurality of kinds of ion species in accordance with the irradiation parameter data 67 by an intensity modulated composite ion therapy. As described with FIG. 3(A), FIG. 3(B) shows an example of the case where the front side of the irradiation direction (the part of small depth, upstream side) is irradiated with a heavy ion species, and the back side of the irradiation direction (the part of large depth, downstream side) is irradiated with a light ion species.

As illustrated in the drawing, the charged particle irradiation system 1 keeps gentle distribution of quality (LET) in the target by combining a first ion species irradiation dose 94, a second ion species irradiation dose 95 and a third ion species irradiation dose 96 indicating physical amount of energy for a clinical dose 91 ($D_{clin}$). In the illustrated example, the charged particle irradiation system 1 irradiates the front side of the irradiation direction with oxygen which is a heavy ion species at a proportion larger than those of other ion species to achieve the first ion species irradiation dose 94, irradiates the center or its periphery of the irradiation direction with carbon which is the second heavy ion species at a proportion larger than those of other ion species to achieve the second ion species irradiation dose 95, and irradiates the back side of the irradiation direction with helium which is a lighter ion species than the above at a proportion larger than those of other ion species to achieve the third ion species irradiation dose 96.

In this manner, the charged particle irradiation system 1 can realize a uniform clinical dose distribution in the target while appropriately changing the quality of radiation (particle species and LET) by combining a plurality of kinds of ion species. As a result, the distribution of quality of radiation (LET) in the target can be kept gentle by combination of the plurality of kinds of ion species, and distortions 91a, 91b in the distribution of the clinical dose 91 can be suppressed to low levels even when errors 92a, 92b occur in a RBE 92.

By optimizing the quality distribution by means of the plurality of kinds of ion species in accordance with the radiation sensitivity of normal cells or cancer cells in a tumor, the charged particle irradiation system 1 can kill only the cancer cells while conserving the normal cells.

By using a light ion species for irradiation of a deep site, the charged particle irradiation system 1 can treat a deep site of the body with an accelerator of low acceleration energy. Generally, high acceleration energy is required for a heavy ion species to reach a deep site, however, according to the present invention, a deep site can be treated with low acceleration energy by using a light ion species, and thus the acceleration energy required as a whole can be reduced. Therefore, it is possible to achieve cost reduction and downsizing of the accelerator, which contributes to the spread of the heavy charged particle therapy.

In addition, by using the plurality of kinds of ion species, the charged particle irradiation system 1 can desirably set spatial distribution of not only dose but also quality even in the single field irradiation from one direction, and improve the concentration of dose to the tumor compared with the conventional case using a single ion species. The charged particle irradiation system 1 can provide a therapy that is insusceptible to relative biological effectiveness (RBE) and irradiation, and registration error. The charged particle irradiation system 1 can also provide an effective therapy depending on the difference in radiation sensitivity between normal cells and cancer cells contained in a tumor. The charged particle irradiation system 1 can realize the dose distribution and the quality distribution to be given into the target without necessity of a large-scale apparatus like a rotary gantry.

The present invention is not limited to the configuration of the aforementioned embodiment, but many embodiments are available.

INDUSTRIAL APPLICABILITY

The present invention is applicable to a charged particle irradiation system that radiates a beam of charged particles to a target.

DESCRIPTION OF REFERENCE SIGNS

1: Charged particle irradiation system
2: Ion source
2A: First ion source
2B: Second ion source
2C: Third ion source
4: Linear accelerator
5: Synchrotron
67: Irradiation parameter data
68: Maximum depth data
70: Planning apparatus
71: CPU
72: Memory
73: Planning program

The invention claimed is:

1. A charged particle irradiation system comprising:
an ion source that generates charged particles;
an accelerator that accelerates the charged particles generated by the ion source;
an irradiation device that irradiates a target with the charged particles drawn from the accelerator;
a controlling apparatus that controls operations of the ion source, the accelerator, and the irradiation device; and
an irradiation planning apparatus that determines an irradiation parameter,
wherein the ion source includes a plurality of kinds of ion sources that generate different ion species as the charged particles,
the controlling apparatus comprises:
a current pattern memory that stores current values to be flown in an electromagnet provided in the accelerator, which is defined for each of the ion species; and a multiple ion species irradiation controller that switches a current value to be flown in the electromagnet of the accelerator based on the ion source to be used and a current value with respect to the target stored in the current pattern memory, and radiates a plurality of kinds of the ion species while the plurality of the kinds of the ion species are switched from each other, the charged particle irradiation system irradiates the charged particles in accordance with the irradiation parameter determined by the irradiation planning apparatus, and the irradiation planning apparatus determines the irradiation parameter for irradiation of the charged particles with respect to the target, wherein the irradiation is conducted while varying a kind of ion species to be radiated to an irradiation spot, which is a stop position of the charged particles, at each site of the target, or varying a ratio between the plurality of the kinds of the ion species to be radiated to the irradiation spot at each site of the target, or varying a combination thereof.

2. The charged particle irradiation system according to claim 1, wherein the irradiation planning apparatus determines the irradiation parameter of the charged particle irradiation system that radiates the charged particles generated by the ion source to the target by accelerating the charged particles by the accelerator, the irradiation planning apparatus comprising:

a CPU, which determines the irradiation parameter for irradiation with respect to the target, wherein the irradiation is conducted while varying the kind of the ion species to be radiated to the irradiation spot from one kind to other kind of the plurality of the kinds of the ion species, and varying the ratio between the plurality of the kinds of the ion species to be radiated to the irradiation spot from site to site in the target, where an irradiation spot radiated with a single kind of the ion species may coexist with the irradiation spot radiated with the plurality of the kinds of the ion species, within the site to site in the target.

3. The charged particle irradiation system according to claim 1, wherein the irradiation planning apparatus comprises:

a memory that stores maximum depth data defining a maximum depth for at least part of the ion species, and a CPU that determines the ion species to be radiated to the stop position located deeper than the maximum depth, where the ion species to be radiated to the stop position located deeper than the maximum depth is an ion species other than the ion species for which the maximum depth is defined.

4. The charged particle irradiation system according to claim 1, wherein the irradiation planning apparatus comprises a CPU that is configured to execute a repetitive operation that determines a preferred one of the irradiation parameter, and the CPU includes a mathematical formula of an evaluation index for an evaluating preference of the irradiation parameter, where the mathematical formula includes a formula that calculates a dose of radiation by the charged particles of the plurality of the kinds of the ion species for each the irradiation spot in the target.

5. The charged particle irradiation system according to claim 1, wherein the irradiation planning apparatus comprises a CPU that is configured to define a plurality of irradiation spots for the target by three-dimensional positions, and to make determination of the ion species to be abundantly radiated to an irradiation spot on a back side of irradiation lighter than the ion species to be radiated to an irradiation spot on a front side of the irradiation.

6. The charged particle irradiation system according to claim 1, wherein the system further comprises a computer comprising an irradiation planning program with which the computer functions as the irradiation planning apparatus that determines the irradiation parameter, the irradiation parameter is a parameter of the charged particle irradiation system that radiates the charged particles generated by the ion source to the target by accelerating the charged particles by the accelerator, the computer comprises a CPU that determines the irradiation parameter for irradiation with respect to the target, wherein the irradiation is conducted while varying the kind of the ion species to be radiated to the irradiation spot from one kind to other kind of the plurality of the kinds of the ion species, and varying the ratio between the plurality of the kinds of the ion species to be radiated to the irradiation spot from site to site in the target, where an irradiation spot radiated with a single kind of the ion species may coexist with the irradiation spot radiated with the plurality of the kinds of the ion species, within the site to site in the target.

7. An operation method for treating a tumor with the charged particle irradiation system according to claim 1, comprising:

irradiating the charged particles generated by the plurality of the kinds of the ion sources to the target by accelerating the charged particles by the accelerator, according to the irradiation parameter determined by the irradiation planning apparatus.

8. The charged particle irradiation system according to claim 1, wherein the plurality of the kinds of the ion species is at least two ion species selected from the group consisting of oxygen ions, carbon ions, and helium ions.

* * * * *